US012797621B2

(12) United States Patent
Leigh et al.

(10) Patent No.: US 12,797,621 B2
(45) Date of Patent: Nov. 17, 2026

(54) WEARABLE DEVICE HEAT MANAGEMENT

(71) Applicant: Cochlear Limited, Macquarie University (AU)

(72) Inventors: Charles Roger Aaron Leigh, North Epping (AU); Oliver John Ridler, Cherrybrook (AU); Martin Joseph Svehla, Botany (AU)

(73) Assignee: Cochlear Limited, Macquarie University (AU)

( * ) Notice: Subject to any disclaimer, the term of this patent is extended or adjusted under 35 U.S.C. 154(b) by 328 days.

(21) Appl. No.: 18/708,880

(22) PCT Filed: Oct. 31, 2022

(86) PCT No.: PCT/IB2022/060476
§ 371 (c)(1),
(2) Date: May 9, 2024

(87) PCT Pub. No.: WO2023/089428
PCT Pub. Date: May 25, 2023

(65) Prior Publication Data
US 2026/0158284 A1 Jun. 11, 2026

Related U.S. Application Data

(60) Provisional application No. 63/279,705, filed on Nov. 16, 2021.

(51) Int. Cl.
*A61N 1/375* (2006.01)
*A61N 1/36* (2006.01)
*A61N 1/378* (2006.01)

(52) U.S. Cl.
CPC ......... *A61N 1/375* (2013.01); *A61N 1/36038* (2017.08); *A61N 1/3787* (2013.01)

(58) Field of Classification Search
CPC .............. A61N 1/36038; A61N 1/3787; A61N 1/0541; A61N 2005/007; A61M 2205/3368; H02J 2105/46; H02J 50/10; H02J 50/80
See application file for complete search history.

(56) References Cited

U.S. PATENT DOCUMENTS 4,921,041 A 5/1990 Akachi
5,692,380 A 12/1997 Cox et al.
(Continued)

FOREIGN PATENT DOCUMENTS

EP 2562200 A1 2/2013
JP 2015071662 A 4/2015
(Continued)

OTHER PUBLICATIONS

Davids, Surur, "Microsoft invented a flexible heat pipe just for the HoloLens," Jan. 15, 2017, https://mspoweruser.com/microsoft-invented-flexible-heat-pipe-just-hololens/, 6 pages.
(Continued)

*Primary Examiner* — Mandeep S Buttar
(74) *Attorney, Agent, or Firm* — Edell, Shapiro & Finnan, LLC

(57) ABSTRACT

Presented herein are techniques for managing heat generated by a wearable device, such as an external component of an implantable device system. The wearable device is configured to be worn by a user and operates within an insulated environment. The techniques presented herein use one or more thermally conductive members to receive heat generated by the wearable device and to transfer heat from the wearable device to a location outside of the insulated environment.

25 Claims, 12 Drawing Sheets

(56) References Cited

U.S. PATENT DOCUMENTS

| | | | | |
|---|---|---|---|---|
| 8,591,562 | B2 * | 11/2013 | D'Ambrosio | A61F 7/12<br>607/45 |
| 10,258,804 | B2 * | 4/2019 | Scott | A61B 5/01 |
| 10,517,755 | B2 * | 12/2019 | D'Ambrosio | A61F 7/10 |
| 10,520,996 | B2 | 12/2019 | Osterhout et al. | |
| 10,576,276 | B2 * | 3/2020 | Leigh | A61N 1/08 |
| 10,888,706 | B2 | 1/2021 | Stinauer et al. | |
| 10,941,251 | B2 | 3/2021 | Appukuttan et al. | |
| 2006/0183965 | A1 * | 8/2006 | Kasic, II | H04R 25/554<br>600/25 |
| 2009/0082832 | A1 | 3/2009 | Carbunaru et al. | |
| 2009/0112278 | A1 * | 4/2009 | Wingeier | A61B 5/4076<br>607/45 |
| 2012/0197341 | A1 | 8/2012 | Cowley et al. | |
| 2012/0326948 | A1 | 12/2012 | Crocco et al. | |
| 2015/0196765 | A1 | 7/2015 | Marnfeldt et al. | |
| 2018/0055500 | A1 | 3/2018 | Scott et al. | |
| 2018/0098903 | A1 | 4/2018 | Vergara et al. | |
| 2018/0163113 | A1 | 6/2018 | Uta et al. | |
| 2018/0356156 | A1 | 12/2018 | Hurbi et al. | |
| 2019/0339528 | A1 | 11/2019 | Freeman et al. | |
| 2021/0194289 | A1 | 6/2021 | Schulzetenberg et al. | |
| 2023/0324965 | A1 | 10/2023 | Yang et al. | |
| 2024/0024156 | A1 | 1/2024 | Vavelin et al. | |
| 2024/0123239 | A1 | 4/2024 | Eder et al. | |

FOREIGN PATENT DOCUMENTS

| | | | |
|---|---|---|---|
| KR | 10-2008-0074291 | A | 8/2008 |
| WO | 2011-119352 | A1 | 9/2011 |
| WO | 2018-222275 | A1 | 12/2018 |
| WO | 2019-195866 | A1 | 10/2019 |
| WO | 2020-172500 | A1 | 8/2020 |

OTHER PUBLICATIONS

International Search Report and Written Opinion in counterpart International Application No. PCT/IB2022/060476, mailed Feb. 10, 2023, 8 pages.

Thermal grizzly, "Minus Pad 8", High Performance Cooling Solutions, Product No. S-TG-MP8-30-30-05-1R, https://www.thermal-grizzly.com/en/Minus-Pad-8/S-TG-MP8, accessed May 8, 2024, 3 pages.

Koppers Inc., "KFOAM", Product Brochure 2013, https://web.archive.org/web/20151021043848/http://www.koppers.com/media/W1siZilsljlwMTQvMDYvMzAvMTJfMjZfNTIfODk1X0tGT0FNUHJVZHVjdEJyb2NodXJIXzlwMTMucGRml11d/KFOAMProductBrochure_2013.pdf?sha=9079e2ce#:~:text=KFOAM%C2%AE%20is%20processed%20to,form%20a%20graphite%20foam%20structure.&text=This%20aligned%20graphite%20structure%20%28formed,the%20foam%.

* cited by examiner

700

WEARABLE DEVICE HEAT MANAGEMENT

BACKGROUND

Field of the Invention

The present invention relates generally to systems and methods for managing heat generated by a wearable device located within an insulated environment.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, an accessory device for an external component is provided. The external component is configured to transfer power to an implantable device, and the external component is configured to be at least partially located within an insulated environment abutting a body of a user. The accessory device comprises: a thermally conductive main body configured to be positioned abutting a housing of the external component within the insulated environment to receive heat generated by the external component; and a thermally conductive extension extending from the thermally conductive main body, wherein the thermally conductive extension is configured to transfer heat from the main body to a location outside of the insulated environment.

In another aspect, an apparatus is provided. The apparatus comprises: a thermally conductive member having at least a thermally conductive first part configured to be in contact with a housing of an external charger that is configured to be worn by a user and transfer power to an implantable device, wherein use of the external charger thermally insulates the housing of the external charger between a body of a user and a covering member, wherein the thermally conductive member comprises at least a thermally conductive second part configured to transfer heat from the thermally conductive first part to a non-insulated environment outside of the covering member.

In yet another aspect, a method is provided. The method comprises: positioning a thermally conductive body abutting a wearable device, wherein the wearable device is configured to be worn by a user, and wherein, when worn by the user, the wearable device is placed in a thermally insulated environment abutting a body of the user; receiving, by the thermally conductive body, heat generated by the wearable device during operation of the wearable device; transferring the heat from the thermally conductive body to a thermally conductive extension that includes a portion located outside of the thermally insulated environment; and expelling the heat received from the thermally conductive body to a location outside of the thermally insulated environment.

In another aspect, an accessory device for wearable device is provided. When worn by a user, the wearable device is configured to be at least partially located within an insulated environment abutting a body of the user, and the accessory device comprises: a thermally conductive main body configured to be positioned abutting a housing of the wearable device within the insulated environment to receive heat generated by the wearable device; and a thermally conductive extension extending from the thermally conductive main body, wherein the thermally conductive extension is configured to transfer heat from the main body to a location outside of the insulated environment.

In another aspect, an accessory device for an external component that is configured to transfer power to an implantable device, wherein the external component is configured to be at least partially located within an insulated environment abutting a body of a user. The accessory device comprises: a thermally conductive main body configured to be positioned abutting a housing of the external component within the insulated environment to receive heat generated by the external component; and a thermally conductive extension extending from the thermally conductive main body, wherein the thermally conductive extension is configured to transfer heat from the main body to a location outside of the insulated environment, wherein the accessory device is physically separate and comprises a headband attached to at least one of the thermally conductive main body or the thermally conductive extension, wherein the headband is formed from a thermally conductive material, wherein at least one of the thermally conductive main body or the thermally conductive extension comprises a thermally conductive foam or one or more heat pipes, and wherein at least one of the thermally conductive main body or the thermally conductive extension comprises an electrically non-conductive material.

BRIEF DESCRIPTION OF THE DRAWINGS

Embodiments of the present invention are described herein in conjunction with the accompanying drawings, in which.

DETAILED DESCRIPTION

Presented herein are techniques for managing heat generated by a wearable device, such as an external component of an implantable device, such as an implantable medical device. The wearable device is configured to be worn by a user and operates within an insulated environment. The techniques presented herein use one or more thermally conductive members to receive heat generated by the wearable device and to transfer heat from the wearable device to a location outside of the insulated environment.

Merely for ease of description, the techniques presented herein are primarily described with reference to a wearable device associated with a specific implantable medical device, namely a cochlear implant. However, it is to be appreciated that the techniques presented herein may also be partially or fully implemented by other types of wearable devices useable with a variety of implantable devices. For example, the techniques presented herein may be implemented by wearable devices associated with other auditory prosthesis systems that include one or more other types of auditory prostheses, such as middle ear auditory prostheses, bone conduction devices, direct acoustic stimulators, electro-acoustic prostheses, auditory brain stimulators, combinations or variations thereof, etc. The techniques presented herein may also be implemented by hearing aids, dedicated tinnitus therapy devices and/or tinnitus therapy device systems. In further embodiments, the presented herein may also be implemented by, or used in conjunction with, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, implantable self-powered tags, implantable tracking devices, etc., which serve no medical/therapeutic purpose, etc.

Figure 1A:
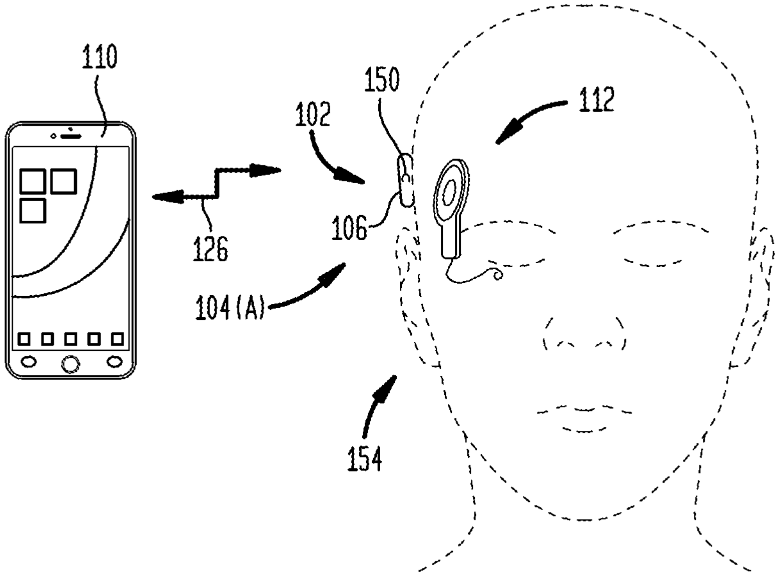
FIG. 1A is a schematic diagram illustrating a cochlear implant system with which aspects of the techniques presented herein can be implemented.
Figure 1B:
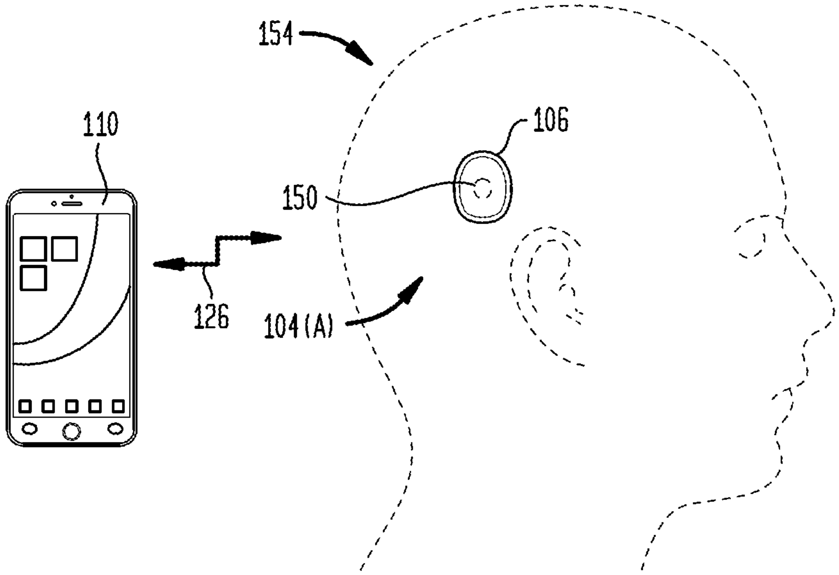
FIG. 1B is a side view of a user wearing a sound processing unit of the cochlear implant system of FIG. 1A.
Figure 1C:
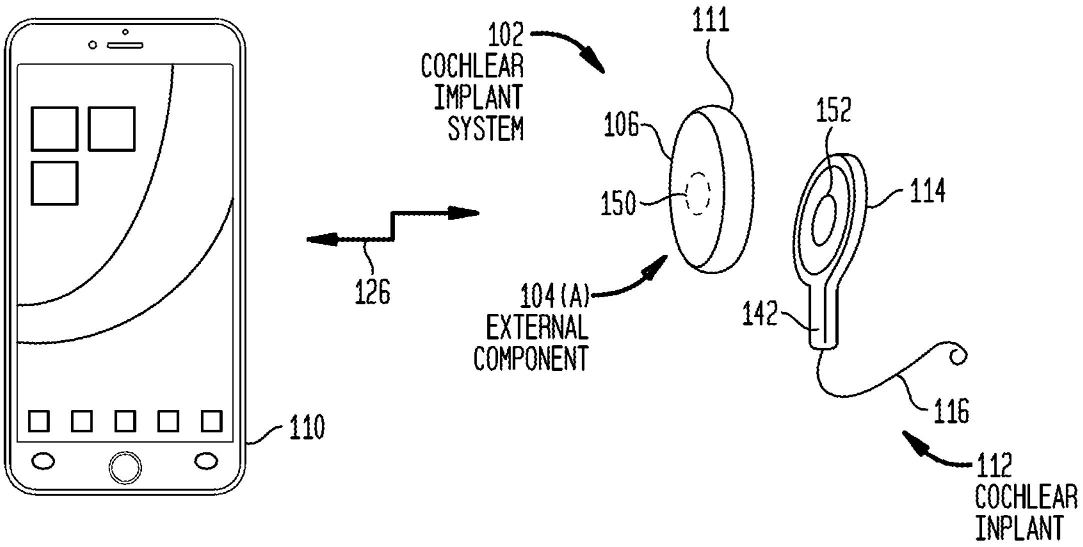
FIG. 1C is a schematic diagram illustrating components of the cochlear implant system of FIG. 1A.
Figure 1D:
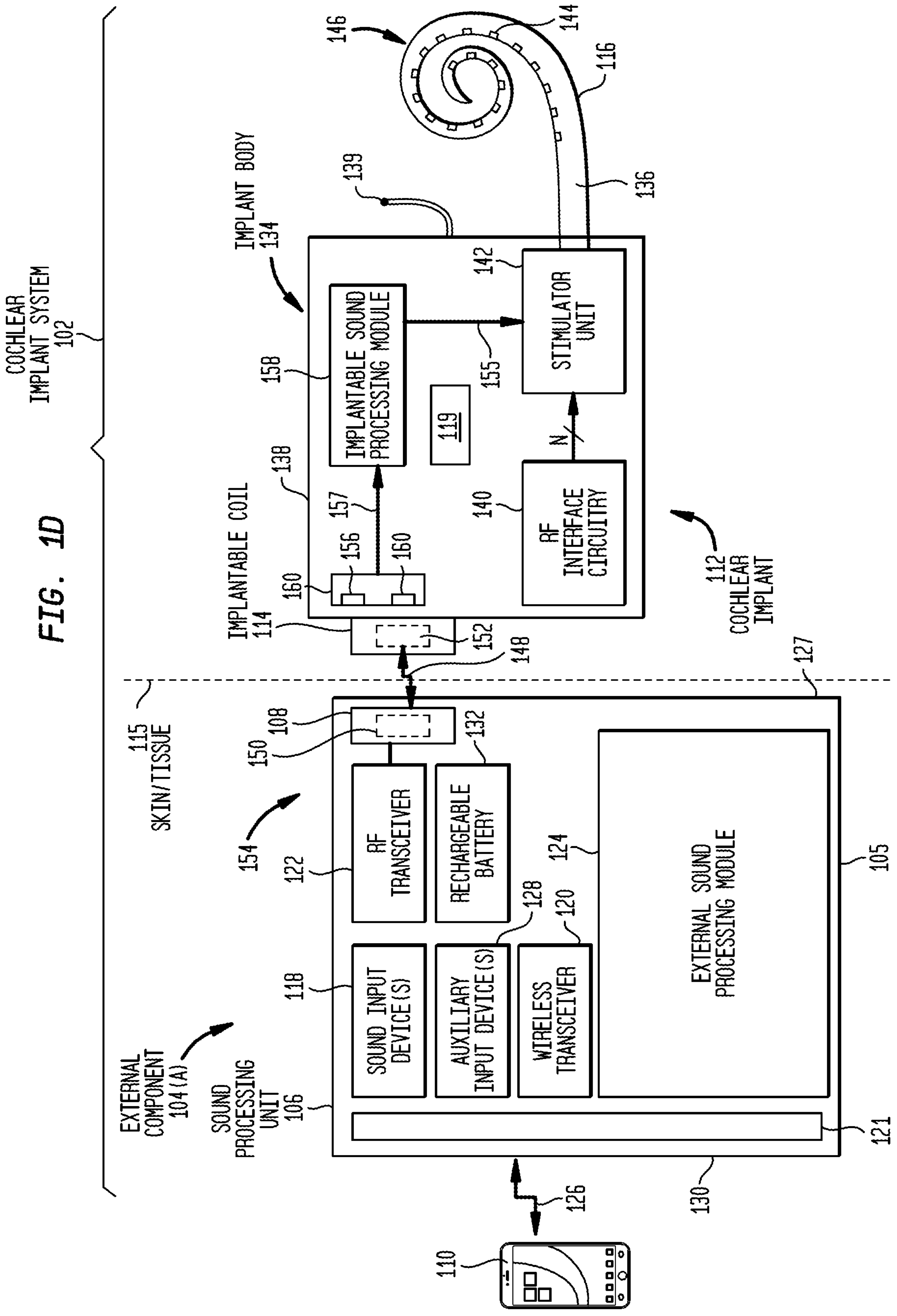
FIG. 1D is a block diagram of the cochlear implant system of FIG. 1A.

FIGS. 1A-1D illustrates an example cochlear implant system 102 with which aspects of the techniques presented herein can be implemented. The cochlear implant system 102 comprises an external component 104(A) and an implantable component 112. In the examples of FIGS. 1A-1D, the implantable component is sometimes referred to as a "cochlear implant." FIG. 1A illustrates the cochlear implant 112 implanted in the head 154 of a user, while FIG. 1B is a schematic drawing of the external component 104(A) worn on the head 154 of the user. FIG. 1C is another schematic view of the cochlear implant system 102, while FIG. 1D illustrates further details of the cochlear implant system 102. For ease of description, FIGS. 1A-1D will generally be described together.

Cochlear implant system 102 includes an external component 104(A) that is configured to be directly or indirectly attached to the body of the user and an implantable component 112 configured to be implanted in the user. In the examples of FIGS. 1A-1D, the external component 104(A) comprises a sound processing unit 106, while the cochlear implant 112 includes an implantable coil 114, an implant body 134, and an elongate stimulating assembly 116 configured to be implanted in the user's cochlea.

In the example of FIGS. 1A-1D, the sound processing unit 106 is an off-the-ear (OTE) sound processing unit, sometimes referred to herein as an OTE component, which is configured to send data and power to the implantable component 112. In general, an OTE sound processing unit is a component having a generally cylindrically shaped housing 111 and which is configured to be magnetically coupled to the user's head (e.g., includes an integrated external magnet 150 configured to be magnetically coupled to an implantable magnet 152 in the implantable component 112). The OTE sound processing unit 106 also includes an integrated external (headpiece) coil 108 that is configured to be inductively coupled to the implantable coil 114.

It is to be appreciated that the OTE sound processing unit 106 is merely illustrative of the external devices that could operate with implantable component 112. For example, in alternative examples, the external component may comprise a behind-the-ear (BTE) sound processing unit or a micro-BTE sound processing unit and a separate external. In general, a BTE sound processing unit comprises a housing that is shaped to be worn on the outer ear of the user and is connected to the separate external coil assembly via a cable, where the external coil assembly is configured to be magnetically and inductively coupled to the implantable coil 114. It is also to be appreciated that alternative external components could be located in the user's ear canal, worn on the body, etc.

As noted above, the cochlear implant system 102 includes the sound processing unit 106 and the cochlear implant 112. However, as described further below, the cochlear implant 112 can operate independently from the sound processing unit 106, for at least a period, to stimulate the user. For example, the cochlear implant 112 can operate in a first general mode, sometimes referred to as an "external hearing mode," in which the sound processing unit 106 captures sound signals which are then used as the basis for delivering stimulation signals to the user. The cochlear implant 112 can also operate in a second general mode, sometimes referred as an "invisible hearing" mode, in which the sound processing unit 106 is unable to provide sound signals to the cochlear implant 112 (e.g., the sound processing unit 106 is not present, the sound processing unit 106 is powered-off, the sound processing unit 106 is malfunctioning, etc.). As such, in the invisible hearing mode, the cochlear implant 112 captures sound signals itself via implantable sound sensors and then uses those sound signals as the basis for delivering stimulation signals to the user. Further details regarding operation of the cochlear implant 112 in the external hearing mode are provided below, followed by details regarding operation of the cochlear implant 112 in the invisible hearing mode. It is to be appreciated that reference to the external hearing mode and the invisible hearing mode is merely illustrative and that the cochlear implant 112 could also operate in alternative modes.

In FIGS. 1A and 1C, the cochlear implant system 102 is shown with an external device 110, configured to implement aspects of the techniques presented. The external device 110 is a computing device, such as a computer (e.g., laptop, desktop, tablet), a mobile phone, remote control unit, etc. As described further below, the external device 110 comprises a telephone enhancement module that, as described further below, is configured to implement aspects of the auditory rehabilitation techniques presented herein for independent telephone usage. The external device 110 and the cochlear implant system 102 (e.g., OTE sound processing unit 106 or the cochlear implant 112) wirelessly communicate via a bi-directional communication link 126. The bi-directional communication link 126 may comprise, for example, a short-range communication, such as Bluetooth link, Bluetooth Low Energy (BLE) link, a proprietary link, etc.

Returning to the example of FIGS. 1A-1D, the OTE sound processing unit 106 comprises one or more input devices that are configured to receive input signals (e.g., sound or data signals). The one or more input devices include one or more sound input devices 118 (e.g., one or more external microphones, audio input ports, telecoils, etc.), one or more auxiliary input devices 128 (e.g., audio ports, such as a Direct Audio Input (DAI), data ports, such as a Universal Serial Bus (USB) port, cable port, etc.), and a wireless transmitter/receiver (transceiver) 120 (e.g., for communication with the external device 110). However, it is to be appreciated that one or more input devices may include additional types of input devices and/or less input devices (e.g., the wireless short range radio transceiver 120 and/or one or more auxiliary input devices 128 could be omitted).

The OTE sound processing unit 106 also comprises the external coil 108, a charging coil 130, a closely-coupled transmitter/receiver (RF transceiver) 122, sometimes referred to as or radio-frequency (RF) transceiver 122, at least one rechargeable battery 132, and an external sound processing module 124. The external sound processing module 124 may comprise, for example, one or more processors and a memory device (memory) that includes sound processing logic. The memory device may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors are, for example, microprocessors or microcontrollers that execute instructions for the sound processing logic stored in memory device.

The implantable component 112 comprises an implant body (main module) 134, a lead region 136, and the intra-cochlear stimulating assembly 116, all configured to be implanted under the skin/tissue (tissue) 115 of the user. The implant body 134 generally comprises a hermetically-sealed housing 138 in which RF interface circuitry 140, at least one rechargeable battery 119, and a stimulator unit 142 are disposed. The implant body 134 also includes the internal/implantable coil 114 that is generally external to the housing 138, but which is connected to the RF interface circuitry 140 via a hermetic feedthrough (not shown in FIG. 1D).

As noted, stimulating assembly 116 is configured to be at least partially implanted in the user's cochlea. Stimulating assembly 116 includes a plurality of longitudinally spaced intra-cochlear electrical stimulating contacts (electrodes) 144 that collectively form a contact or electrode array 146 for delivery of electrical stimulation (current) to the user's cochlea.

Stimulating assembly 116 extends through an opening in the user's cochlea (e.g., cochleostomy, the round window, etc.) and has a proximal end connected to stimulator unit 142 via lead region 136 and a hermetic feedthrough (not shown in FIG. 1D). Lead region 136 includes a plurality of conductors (wires) that electrically couple the electrodes 144 to the stimulator unit 142. The implantable component 112 also includes an electrode outside of the cochlea, sometimes referred to as the extra-cochlear electrode (ECE) 139.

As noted, the cochlear implant system 102 includes the external coil 108 and the implantable coil 114. The external magnet 152 is fixed relative to the external coil 108 and the implantable magnet 152 is fixed relative to the implantable coil 114. The magnets fixed relative to the external coil 108 and the implantable coil 114 facilitate the operational alignment of the external coil 108 with the implantable coil 114. This operational alignment of the coils enables the external component 104(A) to transmit data and power to the implantable component 112 via a closely-coupled wireless link 148 formed between the external coil 108 and the implantable coil 114. In certain examples, the closely-coupled wireless link 148 is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 106 includes the external sound processing module 124. The external sound processing module 124 is configured to convert received input signals (received at one or more of the input devices) into output signals for use in stimulating a first ear of a user (i.e., the external sound processing module 124 is configured to perform sound processing on input signals received at the sound processing unit 106). Stated differently, the one or more processors in the external sound processing module 124 are configured to execute sound processing logic in memory to convert the received input signals into output signals that represent electrical stimulation for delivery to the user.

As noted, FIG. 1D illustrates an embodiment in which the external sound processing module 124 in the sound processing unit 106 generates the output signals. In an alternative embodiment, the sound processing unit 106 can send less processed information (e.g., audio data) to the implantable component 112 and the sound processing operations (e.g., conversion of sounds to output signals) can be performed by a processor within the implantable component 112.

Returning to the specific example of FIG. 1D, the output signals are provided to the RF transceiver 122, which transcutaneously transfers the output signals (e.g., in an encoded manner) to the implantable component 112 via external coil 108 and implantable coil 114. That is, the output signals are received at the RF interface circuitry 140 via implantable coil 114 and provided to the stimulator unit 142. The stimulator unit 142 is configured to utilize the output signals to generate electrical stimulation signals (e.g., current signals) for delivery to the user's cochlea. In this way, cochlear implant system 102 electrically stimulates the user's auditory nerve cells, bypassing absent or defective hair cells that normally transduce acoustic vibrations into neural activity, in a manner that causes the user to perceive one or more components of the received sound signals.

As detailed above, in the external hearing mode the cochlear implant 112 receives processed sound signals from the sound processing unit 106. However, in the invisible hearing mode, the cochlear implant 112 is configured to capture and process sound signals for use in electrically stimulating the user's auditory nerve cells. In particular, as shown in FIG. 1D, the cochlear implant 112 includes a plurality of implantable sound sensors 160 and an implantable sound processing module 158. Similar to the external sound processing module 124, the implantable sound processing module 158 may comprise, for example, one or more processors and a memory device (memory) that includes sound processing logic. The memory device may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors are, for example, microprocessors or microcontrollers that execute instructions for the sound processing logic stored in memory device.

In the invisible hearing mode, the implantable sound sensors 153, 156, 160 are configured to detect/capture signals (e.g., acoustic sound signals, vibrations, etc.), which are provided to the implantable sound processing module 158. The implantable sound processing module 158 is configured to convert received input signals 157 (received at one or more of the implantable sound sensors 153, 156, 160) into output signals 155 for use in stimulating the first ear of a user (i.e., the processing module 158 is configured to perform sound processing operations). Stated differently, the one or more processors in implantable sound processing module 158 are configured to execute sound processing logic in memory to convert the received input signals 157 into output signals 155 that are provided to the stimulator unit 142. The stimulator unit 142 is configured to utilize the output signals 155 to generate electrical stimulation signals (e.g., current signals) for delivery to the user's cochlea, thereby bypassing the absent or defective hair cells that normally transduce acoustic vibrations into neural activity. The at least one rechargeable battery 119 can be used to power components of the cochlear implant 112 while operating in the invisible hearing mode and or while operating in the external hearing mode.

It is to be appreciated that the above description of the so-called external hearing mode and the so-called invisible hearing mode are merely illustrative and that the cochlear implant system 102 could operate differently in different embodiments. For example, in one alternative implementation of the external hearing mode, the cochlear implant 112 could use signals captured by the sound input devices 118 and/or the implantable sound sensors 153, 156, 160 in generating stimulation signals for delivery to the user.

Figure 1E:
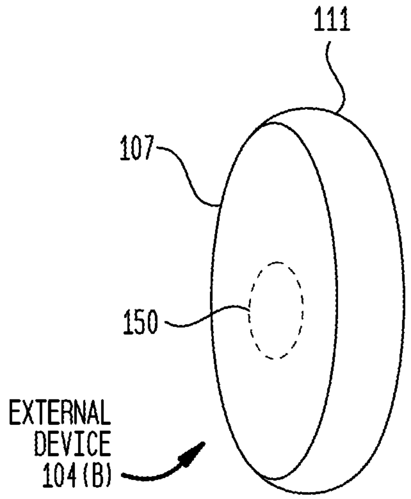
FIG. 1E is schematic diagram illustrating an external charge for use as part of the cochlear implant system of FIG. 1A, in accordance with certain embodiments presented herein.

As noted, FIGS. 1A-1D illustrate an external component 104(A) in the form of an OTE sound processing unit 106. Also as noted above, the OTE sound processing unit 106 can be used to transfer power and data to the cochlear implant 112. In certain circumstances, as shown in FIG. 1E, the cochlear implant system 102 can comprise an alternative external component, referred to herein as external component 104(B). In this example, the external component 104 (B) is an external charger 107 that is configured to transfer power to the cochlear implant 112. In this example, the external charger 107 is similar in shape and size to the OTE sound processing unit 106 and also includes a housing 111, a coil (not shown in FIG. 1E), a power source (e.g., rechargeable battery) (also not shown in FIG. 1E), and a magnet 150 configured to be magnetically coupled to the implantable magnet 152. As such, the external charger 107 can be worn on the head of the user and used to recharge the at least one rechargeable battery 119.

As noted, there are a variety of wearable devices that can be used, for example, with implantable devices and/or used as stand-alone devices. In certain examples, the wearable device is an external component of an implantable device system and is configured to be worn by a user to transcutaneously transfer power (and potentially data) to an implantable component. For example, with specific reference to the embodiments of FIGS. 1A-1D, the OTE sound processing unit 106 or the external charger 107 can be worn on the head of the user and can operate to transcutaneously transfer power to the cochlear implant 112. The OTE sound processing unit 106 or the external charger 107 can be worn while the user is awake and/or while the user is asleep.

In one exemplary embodiment of FIGS. 1A-1E, the at least one rechargeable battery 119 of the cochlear implant 112 is charged while the user is sleeping via the external charger 107 so that the cochlear implant 112 could be powered solely by the at least one rechargeable battery 119 for extended periods of time, such as the entirety of the time the user is awake. The amount of time the external charger 107 charges the at least one rechargeable battery 119 per day/night, per week, or per month is not necessarily limited. In one embodiment, the at least one rechargeable battery 119 only requires one night per week, and the cochlear implant 112 may be powered using the sound processing unit 106 at various other times during the week.

Figure 2:
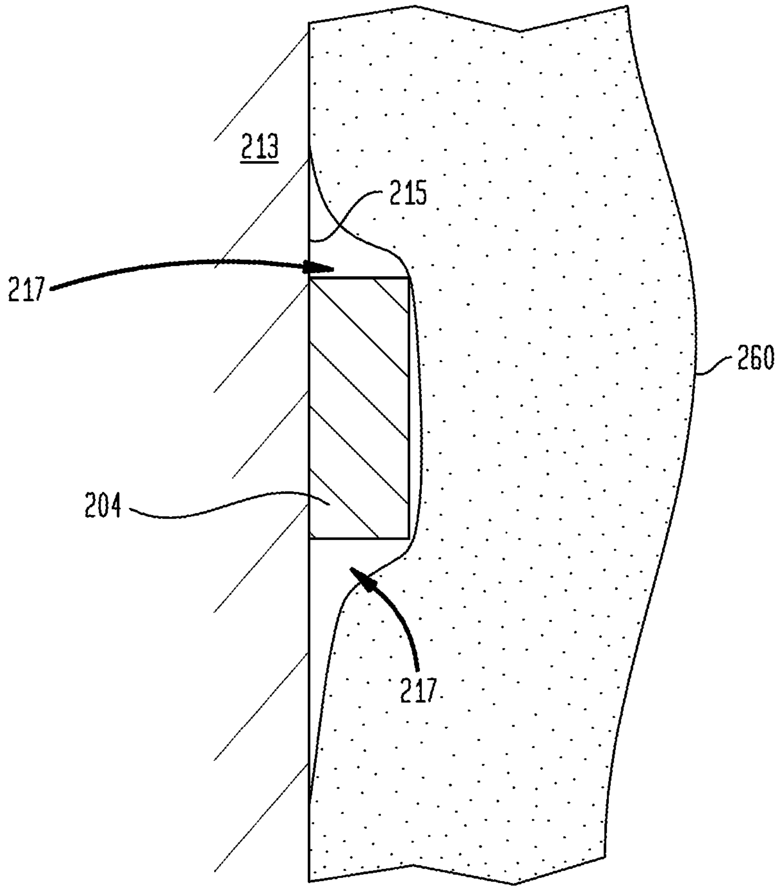
FIG. 2 is a schematic diagram illustrating a prior art system that includes an external component of an implantable device system within an insulated environment.

In certain circumstances, a wearable device, such as an external component of an implantable device system, is worn by a user in an "insulated environment abutting a body of the user." As used herein, an insulated environment abutting a body of a user, or simply insulated environment, refers to a thermally insulated environment in which the wearable device (e.g., external component) is substantially enclosed between the body of the user (e.g., the head, torso, arms, and/or legs of the user) and an insulator (insulating element or material). FIG. 2 shows an example arrangement in which an external component 204 of an example implantable system placed on the skin 215 of a user. The implantable device (not shown in FIG. 2) is configured to be implanted within tissue 213 of the user. An insulator 260, which may be a pillow, head covering, etc. is placed adjacent the external component 204 and thermally encloses the external component 204 (e.g., the external component 204 is enclosed between the user's skin 215 and the insulator 260). This structural configuration creates an insulated environment 217 in which heat generated by the external component 204 will be trapped/collected around the external component 204. The trapped heat within the insulated environment 217 can cause an increase in the temperatures of at least (1) the external component 204, (2) the portion of the skin 215 touching the external component 204, a (3) the portion of the insulator 260 adjacent to the external component 204, etc.

The above-noted structural configuration shown in FIG. 2 can occur, for example, when the external component 204 is worn on the head and user has his or her head on a pillow, the external component 204 is worn on the head and user is wearing a head covering (e.g., hat, scarf, helmet, etc.), etc.

As noted above, when the external component 204 is operating and/or charging the implantable device, the external component 204 generates heat. Because the external component 204 is completely enclosed by the insulator 260, the heat collects in the above-noted insulated environment 217. This arrangement has the inherent problem that the heat generated in the insulated environment may cause discomfort, pain, or injury to a user and/or could detrimentally affect operation of the external component 204.

Presented herein are techniques for managing heat generated by a wearable device, such as an external component of an implantable device system, worn by a user within an insulated environment abutting the body of the user. In particular, the techniques presented herein use one or more thermally conductive members to receive heat generated by the wearable device and to transfer heat from the wearable device to a location outside of the insulated environment. In certain embodiments, the one or more thermally conductive members are embodied as an accessory device for use with a wearable device.

Figure 3A:
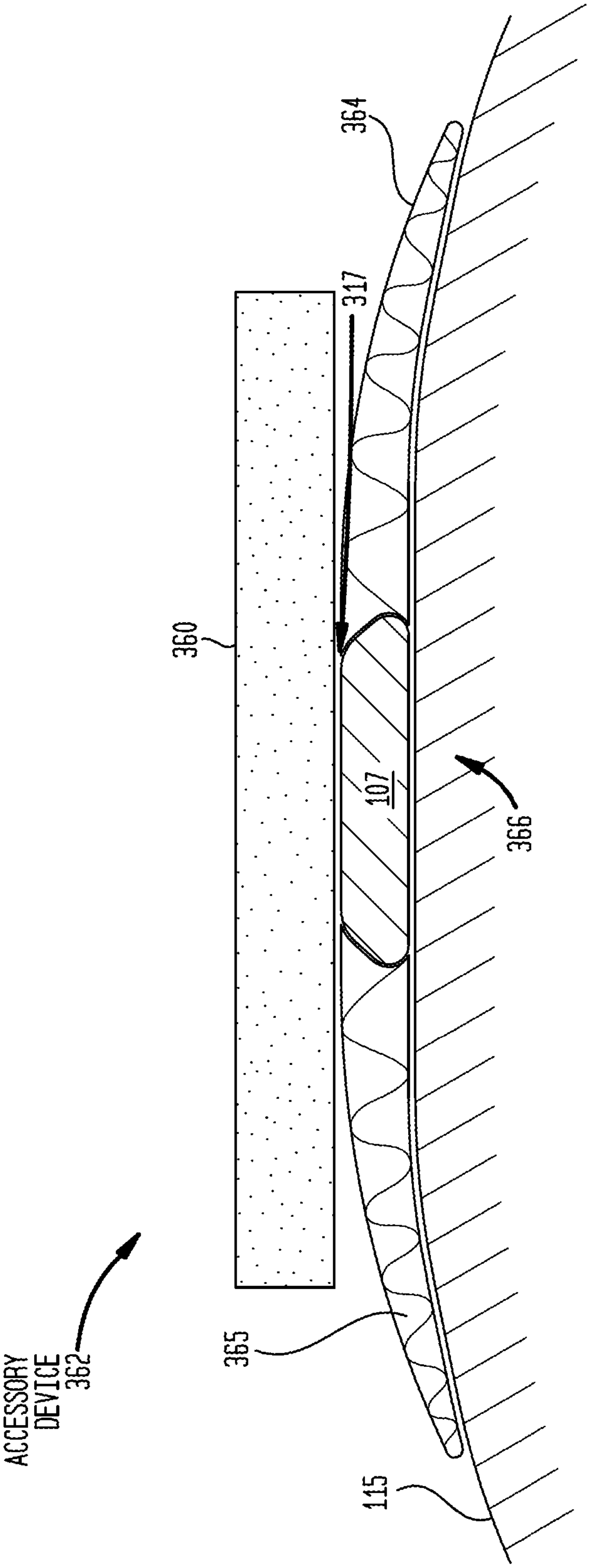
FIG. 3A is a cross-sectional side view of an accessory device, in accordance with certain embodiments presented herein.
Figure 3B:
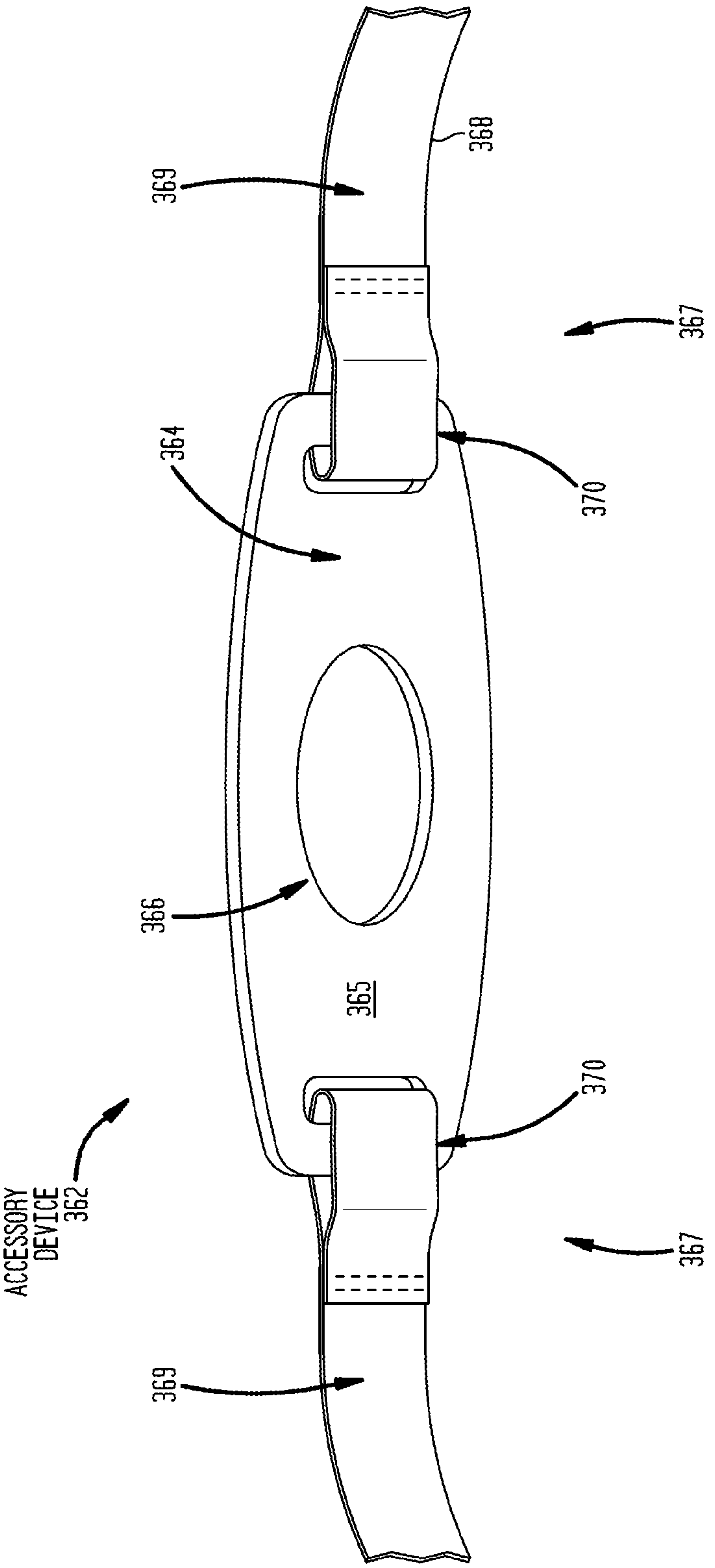
FIG. 3B is a top view of the accessory device of FIG. 3A.

FIG. 3A is a cross-sectional side of an example accessory device 362 configured to transfer heat from a wearable device within an insulated environment, in accordance with certain embodiments presented herein. FIG. 3B is a top view of the accessory device 362 of FIG. 3A. For ease of description, FIGS. 3A and 3B will be described together. Also, for ease of description, the accessory device 362 of FIGS. 3A and 3B will be described in use with a specific wearable device, namely the external charger 107 of FIG. 1E. Reference to external charger 107 is merely illustrative and the embodiments of FIG. 3 could be implemented with a number of different types of wearable devices, including other types of external components of implantable device systems.

As shown, the accessory device 362 comprises a thermally conductive main body (main body) 364 that is configured to be positioned abutting the external charger 107. In this example, the main body 364 is at least partially formed from a thermally conductive material 365 and is configured to be selectively attached to, and removed from, the external charger 107. Specifically, in this example, the main body 364 comprises an opening/aperture 366 into which the external charger 107 can snap, clip, or otherwise fit into. That is, the main body 364 includes an opening or space within the thermally conductive material 365 that is configured to receive and retain the external charger 107.

The thermally conductive material 365 forming at least part of the main body 364 may include, for example, a conductive foam or other elastically deformable conductive material. In an exemplary embodiment shown in FIG. 2B, the thermally conductive material 365 is a conductive foam configured for an interference fit with the external charger 107, when the external charger 107 is placed inside of the opening 366. This interference fit between the thermally conductive material 365 functions as an attachment mechanism to mechanically couple the external charger 107 to the main body 364. In alternative embodiments, other types of attachment mechanisms can be provided to secure the external charger 107 within the opening 107. These attachment mechanisms can take a number of different forms and can include, but are not limited to, a magnetic connections, hook and loop fasteners, snap-fit connections, etc.

As noted, FIGS. 3A and 3B illustrate an embodiment in which the external charger 107 is releasably coupled to the main body 364 (e.g., releasably retained in opening 366). In alternative embodiments, the main body 364 could be irremovably attached to the external charger 107.

Regardless of the attachment mechanism between the main body 364 and the external charger 107, the external charger 107 is configured to be in thermal contact with the thermally conductive material 365 forming at least part of the main body 364. Thermal contact between the thermally conductive material 365 forming at least part of the main body 364 and the external charger 107 can be achieved, e.g., by physical contact between the components.

As shown in FIG. 3B, the accessory device 362 also comprises a thermally conductive extension 367 extending from the thermally conductive main body 364. In this example, the accessory device 362 comprises a headband 368 configured to wrap around the user's head. The headband 368 is in thermal contact with the thermally conductive material 365 of the main body 364 at locations 370. The headband 368 may also include, or be at least partially formed from, a thermally conductive material 369, which may be the same as, or different from, the thermally conductive material 365.

As noted above, the external charger 107 is used to charge the at least one rechargeable battery 119 within the cochlear implant 112. For a medical device, such as cochlear implant 112 configured to be implanted into a user's head (or worn in an orifice in the head of the user), the external charger 107 is also worn on the user's head. As noted above, there is a potential for such devices to, when operating, be located in an "insulated environment abutting a body of a user." Again, as noted above, an insulated environment abutting a body of a user refers to a thermally insulated environment in which the external charger 107 (or other external component) is substantially enclosed between the body of the user (e.g., the head, torso, arms, and/or legs of the user) and an insulator (insulating element or material).

FIG. 3B shows an example arrangement in which an external charger 107 is placed on the skin 115 of a user of the cochlear implant 112 (not shown in FIG. 3B). An insulator 360, which may be a pillow, head covering, etc. is placed adjacent the external charger 107 and thermally encloses the external charger 107 (e.g., the external charger is enclosed between the user's skin 115 and the insulator 360). This structural configuration creates a thermally insulated environment 317 in which heat generated by the external charger 107 could be trapped/collected around the external charger 107. That is, the thermally insulated environment 317 can be formed, for example, when the external charger 107 is worn on the head and user has her head on a pillow, the external charger 107 is worn on the head and user is wearing a head covering (e.g., hat, scarf, burka, hijab, helmet, etc.), etc.

When operating in the thermally insulated environment 317, the external charger 107 generates heat that can become trapped within the thermally insulated environment 317. As noted, trapped heat within an insulated environment can, for example, cause an increase in the temperatures of the external charger 107, cause an increase in temperature of a portion of the skin 115 touching the external charger 107, cause an increase in temperature of a portion of the insulator 260 adjacent to the external charger 107, etc. As such, without a mechanism to transfer the generated heat out of the thermally insulated environment 317, the generated (and trapped) heat may be uncomfortable or dangerous for a user or the external charger 107 itself. In accordance with the embodiments presented herein, the accessory device 362 is configured remediate this issue by transferring or transporting the heat generated by the external charger 107 outside of the insulate environment 317.

More specifically, as noted above and as shown in FIG. 3A, the insulator 360 covers the external charger 107 and at least a portion of the main body 364. That is, the external charger 107 and a portion of the main body 364 are located/disposed within the insulated environment 317. In operation, the thermally conductive material 365 in the main body 364 is configured to receive at least a portion of the heat generated by the external charger 107 during operation thereof (e.g., the thermally conductive material 365 in the main body 364 is in contact with the housing of the external charger). The thermally conductive material 365 in the main body 364 that receives the heat generated by the external charger 107 is within the insulated environment 317, namely abutting the external charger 107. However, as noted, the accessory device 362 also comprises the thermally conductive extension 367 extending from the thermally conductive main body 364, where the thermally conductive extension 367 is configured to transfer heat from the main body 364 to a location outside of the insulated environment 317.

In certain embodiments, the thermally conductive extension 367 comprises a portion of the main body 364 located outside of the insulated environment 317. In other embodiments, the thermally conductive extension 367 comprises the headband 368, where the headband 368 is located outside of the insulated environment. In still other embodiments, the thermally conductive extension 367 comprises both a portion of the main body 364 located outside of the insulated environment 317 and the headband 368.

In general, the heat is transferred to a portion of the main body 364 that is outside of the insulated environment 317 and/or to the thermally conductive material 365 in the headband 368. In other words, the thermally conductive material 365 and/or the thermally conductive material 369 transfers the heat from the external charger 107 and expels the heat received from the external charger 107 to a location outside of the thermally insulated environment 317. The transfer of the heat from within the thermally insulated environment 317 to outside of the thermally insulated environment 317 reduces the potential for an uncomfortable or dangerous situation for the user resulting from the buildup of heat within the thermally insulated environment 317. Heat may be transferred throughout the components the accessory device 362 via, for example, thermal diffusion.

It is to be appreciated that thermally conductive material(s) 365 and 369 of the accessory device 362 are not necessarily limited, and may be any material or combination of materials that effectively transfer heat. The accessory device 362 preferably consists of materials that have a high thermal conductivity and have little or no electrical resistance at least in the portion of the accessory device 362 physically adjacent to the external charger 107. Material(s) with low (or no/negligible) electrical resistance can minimize (or prevent) eddy current loss when transferring energy from the external charger 107 to the cochlear implant 112 via electromagnetic induction. As such, in certain embodiments, the thermally conductive material(s) 365 and 369 could comprise or include materials such as, for example, gold, silver, copper, and/or aluminum. In other embodiments, materials with very low electrical conductivity minimize (or prevent) eddy current loss when transferring energy from the external charger 107 to the cochlear implant 112 via electromagnetic induction (e.g., eddy currents cannot flow through the material, hence there is no eddy current loss). As such, in certain embodiments, the thermally conductive material(s) 365 and 369 could comprise or include materials such as, for example, phonon based thermal conductors.

As noted above, the accessory device 362 preferably includes material(s) with high thermal conductivity and, for example, little to no electrical conductivity. For example, the accessory device 362 may include one or more materials having a high phonon-based thermal conductivity and little to no free electrons such as, e.g., diamonds, other pads/elements based on phonon based thermal conductance. The accessory device 362 may use Aluminum Nitride, and the Aluminum Nitride may be used for a physical interface between the external charger 107 and the accessory device 362. The accessory device 362 may include one or more thermal pads, which may include paraffin wax or silicone and may include metal oxides, etc.

Since many thermally conductive materials are also electrically conductive, the accessory device 362 may include material(s) that have a substantially high thermal conductance and a suitably low electrical conductance. For example, one or more materials of the accessory device 362 may have a thermal conductivity that is above a predetermined thermal conductivity threshold and/or have an electrical conductivity that is below a predetermined electrical conductivity threshold. The accessory device 362 may include a carbon foam or highly orientated graphite foam that meets such criteria. The accessory device 362 may include a composite material, and the composite material may include layers of highly thermally conductive material sandwiched between layers of electrically insulating material. In one exemplary embodiment, the accessory device 362 includes relatively thick layers of highly thermally conductive material sandwiched between relatively thin layers of electrically insulating material.

Figure 4:
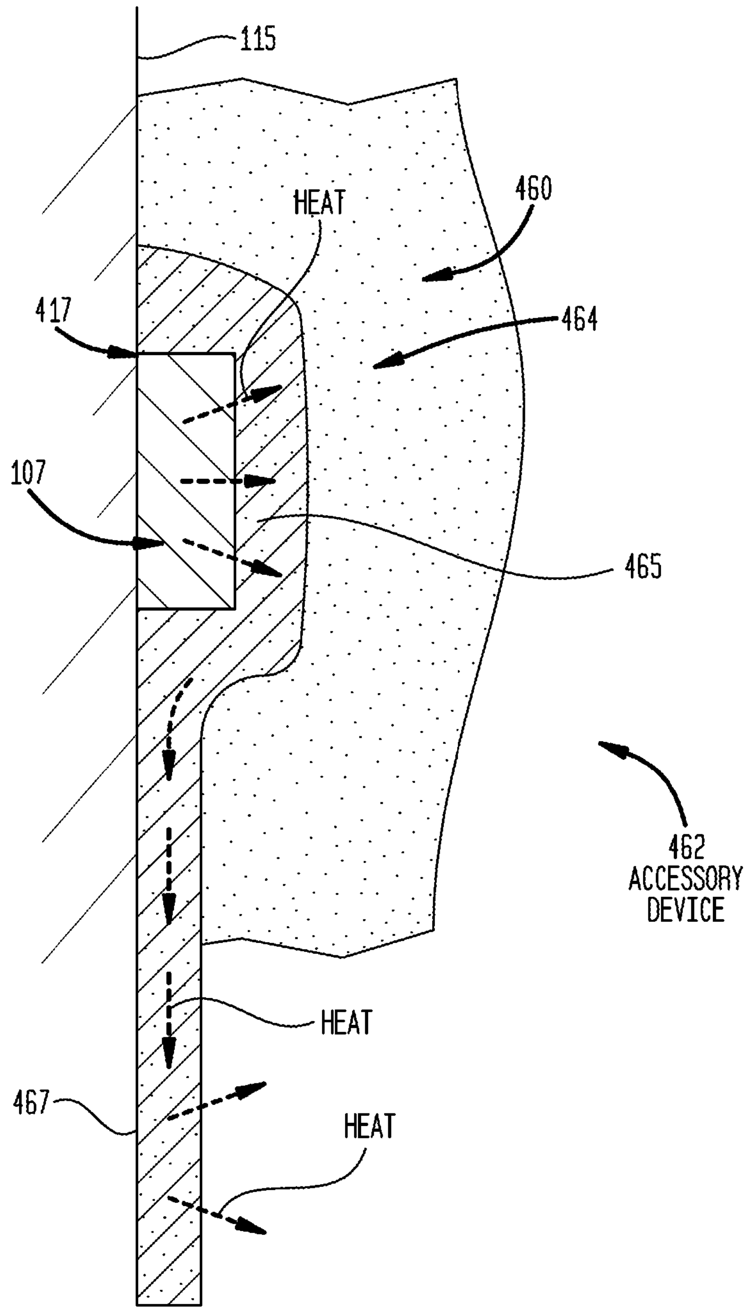
FIG. 4 is a schematic diagram illustrating an accessory device configured to transfer heat generated by an external component of an implantable device system to a location outside of an insulated environment, in accordance with certain embodiments presented herein.

FIG. 4 is a cross-sectional side via of another accessory device 462, in accordance with certain embodiments presented herein. For ease of illustration, the example of FIG. 4 will again be described with reference to external charger 107 of FIG. 1E. As noted, reference to external charger 107 is merely illustrative and the embodiments of FIG. 4 could be implemented with a number of different types of wearable devices, including other external components of implantable device systems.

As noted, the external charger 107 is placed adjacent the user's skin 115 in order to transfer power to the cochlear implant 112 (not shown in FIG. 4). The accessory device 462 is configured to be in thermal contact with the external charger 107 and is configured to transfer heat generated by the external charger 107 to a non-insulated environment.

As shown, the accessory device 462 comprises a thermally conductive main body (main body) 464 that is configured to be positioned abutting the external charger 107, and a thermally conductive extension 467 extending from the thermally conductive main body 464, where the thermally conductive extension 467 is configured to transfer heat from the main body 464. In this example, the main body 464 is at least partially formed from a thermally conductive material 465 and is configured to be selectively attached to, and removed from, the external charger 107. The thermally conductive material 465 forming the main body 464 may include, for example, a conductive foam or other elastically deformable conductive material.

As noted, the thermally conductive material 465 forming at least part of the main body 464 is in thermal contact with the external charger 107. Thermal contact between the thermally conductive material 465 forming at least part of the main body 464 and the external charger 107 can be achieved, e.g., by physical contact between the components. It is to be appreciated that thermally conductive material(s) 465 of the main body 464 are not necessarily limited, and may be any material or combination of materials that effectively transfer heat, such as any of the materials described above with reference to FIGS. 3A and 3B.

In operation, the external charger 107 is placed on the skin 115 of a user and an insulator 460, which may be a pillow, head covering, etc. is placed adjacent the external charger 107 and thermally encloses the external charger 107 (e.g., the external charger is enclosed between the user's skin 115 and the insulator 460). This structural configuration creates an insulated environment 417 in which heat generated by the external charger 107 will be trapped/collected around the external charger 107. As noted above, when operating in the insulated environment 417, the external charger 107 generates heat that can become trapped within the insulated environment 417 which, in turn, could cause an increase in the temperatures of the external charger 107, cause in increase in temperature of a portion of the skin 115 touching the external charger 107, etc. As such, without a mechanism to transfer the generated heat out of the thermally insulated environment 417, the generated (and trapped) heat may be uncomfortable or dangerous for a user or the external charger 107 itself. The accessory device 462 is configured remediate this issue by transferring or transporting the heat generated by the external charger 107 outside of the insulate environment 417.

More specifically, as noted above and as shown in FIG. 4, the insulator 460 covers the external charger 107 and the main body 464. That is, the external charger 107 and the main body 464 are located/disposed within the insulated environment 417. In operation, the thermally conductive material 465 in the main body 464 is configured to receive at least a portion of the heat generated by the external charger 107 during operation thereof. The thermally conductive material 465 in the main body 464 that receives the heat generated by the external charger 107 is within the insulated environment 417, namely abutting the external charger 107. However, the accessory device 462 is configured to transfer the received heat to a location outside of the insulated environment 417.

To this end, the accessory device 462 comprises a thermally conductive extension 467 extending from the thermally conductive main body 464. The thermally conductive extension 467 is configured to transfer heat from the main body 463 to a location outside of the insulated environment 417 (e.g., where the heat transferred to the thermally conductive extension 467 is expelled to an ambient environment outside of the insulated environment.

In the example of FIG. 4, the thermally conductive extension 467 comprises one or more heat pipes. The use of heat pipes at the thermally conductive extension 467 can facilitate efficient transfer of heat and/or facilitate directional control over the transfer of the heat. For example, heat pipes may be included in the thermally conductive extension 467 to efficiently transfer heat from the main body 464. The heat pipe(s) may be flexible heat pipe(s) and/or may be tuned to operate in a temperature range consistent with a human body's temperature such as, e.g., 30-40° Celsius.

Figure 5:
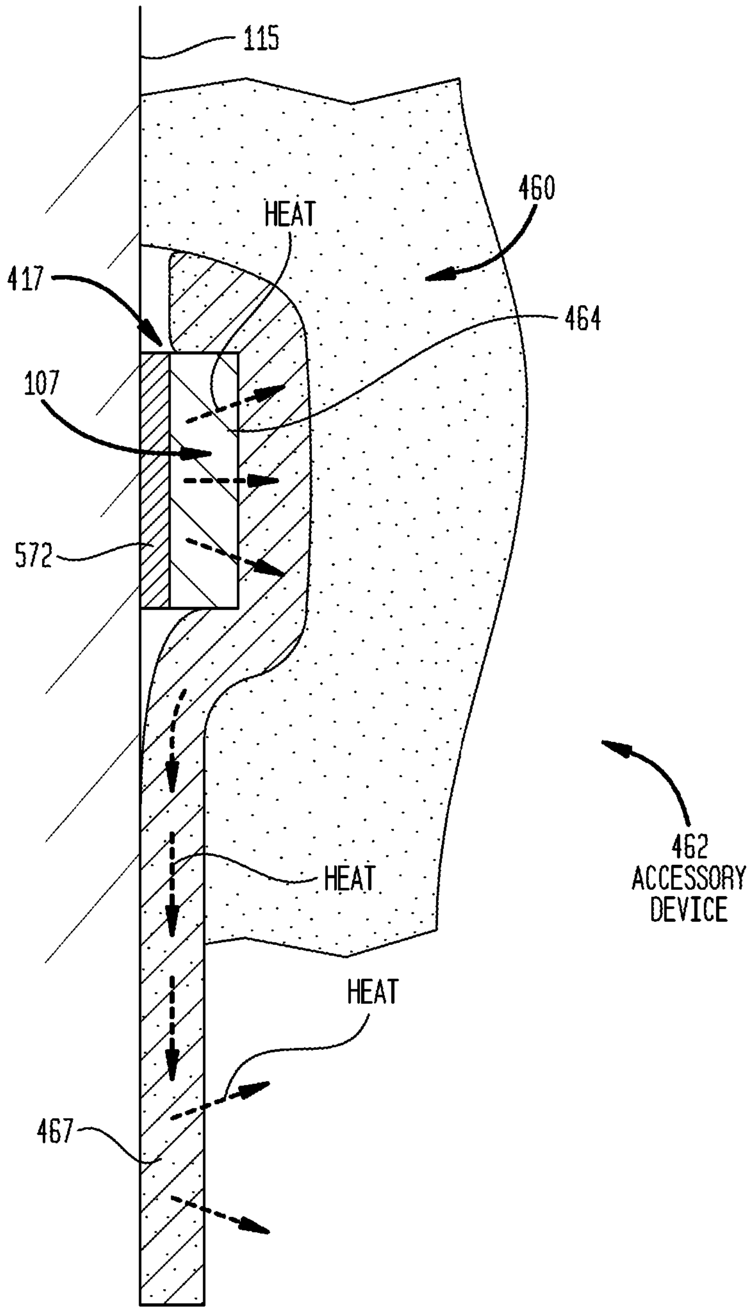
FIG. 5 is a schematic diagram illustrating the accessory device of FIG. 4A with an additional insulator between the skin of a user and the external component of the implantable device system, in accordance with certain embodiments presented herein.

FIG. 5 illustrates an alternative arrangement of that shown in FIG. 4 which includes an additional insulator 572 disposed between the user/user's skin 115 and the external charger 107. The added insulator 572 may minimize or prevent heat transfer to the skin 115 and/or may serve to direct heat transfer from the external charger 107 to the accessory device 462.

FIGS. 3A, 3B, 4, and 5 generally illustrate accessory devices configured to be worn on the head of user. It is to be appreciated that accessory devices in accordance with embodiments presented herein can be configured to be worn on other parts of a user or user's body besides the user or user's head and may be included in any type of clothing, garment, or accessory. The accessory device is preferably worn on or near a location where the external component of an implantable device system, or a wearable external device, is worn by the user. For example, if an external component of an implantable device system or another type of wearable device is configured to be worn on a user's ankle/foot or implanted into a user's ankle/foot, the accessory device may be integrated into, e.g., an ankle brace, ankle bracelet, sock, stocking, boot, shoe, etc. The location on the body on which the accessory device is worn is thus not limited.

Figure 6:
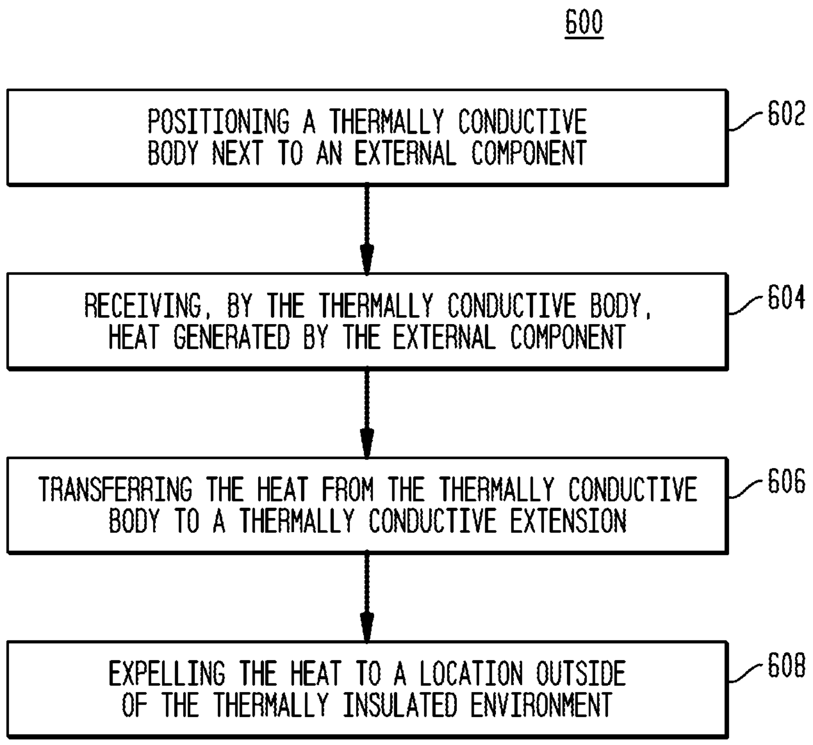
FIG. 6 is a flowchart of an exemplary method, in accordance with certain embodiments presented herein.

FIG. 6 is a flowchart illustrating an exemplary method 600 for managing heat generated by an external component of an implantable 1 device system. At step 602, a thermally conductive body abutting the external component is positioned on a user of the implantable device system. That is, the external component is configured to be worn by a user (e.g., recipient of a medical device) and is configured to transfer power to an implantable device. When worn by the user, the external component is placed in a thermally insulated environment. At step 604, the thermally conductive body receives heat generated by the external component during transfer of power to the implantable device. At step 606, heat is transferred from the thermally conductive body to a thermally conductive extension that includes a portion located outside of the thermally insulated environment. At step 608, the heat received from the main body is expelled to a location outside of the thermally insulated environment.

In certain embodiments, the accessory device is not necessarily a wearable accessory device. For example, the accessory device may be a pillow, or the accessory device may be a pillowcase configured to accept a user/user's pillow. In the case of the accessory device being, e.g., a pillow or a pillowcase, the external device may be a charger incorporated into the pillow or pillowcase.

Figure 7:
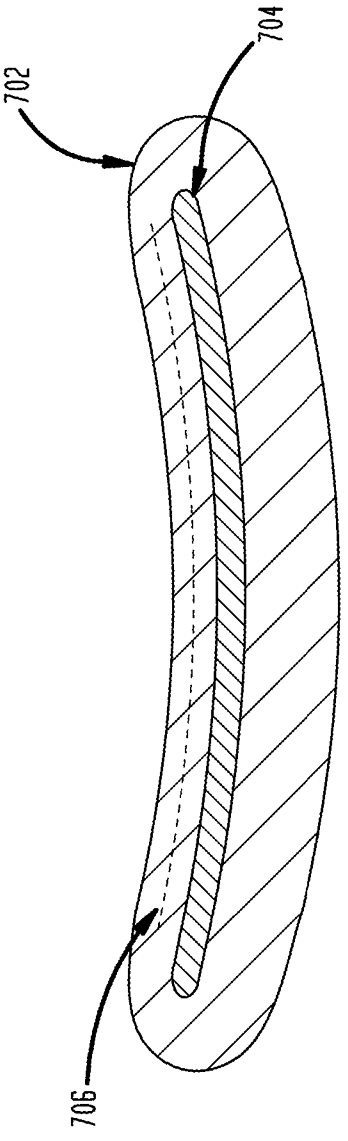
FIG. 7 is a cross-sectional view of a pillow charger, in accordance with certain embodiments presented herein.

FIG. 7 shows an exemplary accessory device 700 that takes the form of a pillow charger or pillowcase charger. In the embodiment shown in FIG. 7, the external charging device is integrated into the accessory device 700. Specifically, the pillow/pillowcase charger accessory device 700 includes a plurality of coils 706 that may inductively couple to a coil included in the medical device. Due to the plurality of coils 706, if the medical device and the accessory device 700 move relative to one another, the accessory device 700 may continue to transfer power to the medical device notwithstanding the relative motion. Accordingly, with the pillow/pillowcase charger 700, a user/user has freedom to adjust a position of the pillow charger or the pillow in which a pillowcase charger is placed, and the accessory device/external device continues to transfer power to the medical device. As such, while a wearable external device may include a magnet configured to be attracted to a magnet in the medical device, the external device of the pillow/pillowcase charger may not include a magnet.

The pillow/pillowcase charger 700 further includes thermally conductive material 704 that is configured to transfer or transmit heat generated as a result of charging the medical device. The thermally conductive material 704 may be inside of the pillow/pillowcase and in thermal contact with the plurality of coils 706.

Accordingly, an accessory device (1) provides a user with protection and increased comfort while resting or sleeping, and (2) enables the ability to charge a user-worn or user-implanted medical device while the user/user rests or sleeps.

As previously described, the technology disclosed herein can be applied in any of a variety of circumstances and with a variety of different devices. That is, as further described below, a variety of different devices can use the heat management systems and methods described above with reference to FIGS. 2-7. For example, the techniques described herein can be used to safely and comfortably charge a vestibular stimulator as described in FIG. 8, a retinal prosthesis, etc. The techniques of the present disclosure can be applied to other medical devices, such as neurostimulators, cardiac pacemakers, cardiac defibrillators, sleep apnea management stimulators, seizure therapy stimulators, tinnitus management stimulators, and vestibular stimulation devices, as well as other medical devices that deliver stimulation to tissue. Further, technology described herein can also be applied to wearable consumer devices. These different systems and devices can benefit from the technology described herein.

Figure 8:
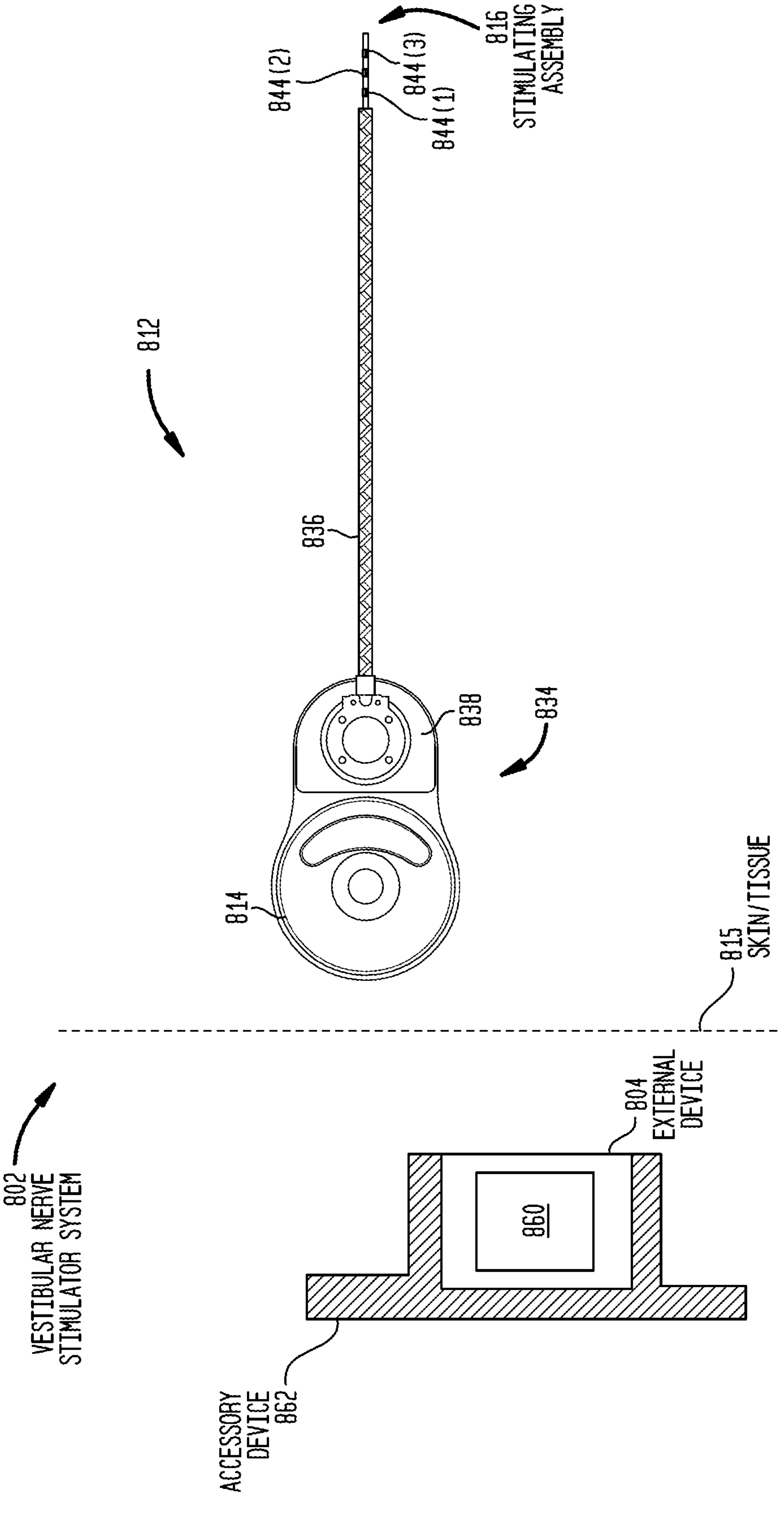
FIG. 8 is a schematic diagram illustrating a vestibular stimulator system with which aspects of the techniques presented herein can be implemented.

FIG. 8 illustrates an example vestibular stimulator system 802, with which embodiments presented herein can be implemented. As shown, the vestibular stimulator system 802 comprises an implantable component (vestibular stimulator) 812 and an external device/component 804 (e.g., external processing device, battery charger, remote control, etc.). The external device 804 comprises a transceiver unit 860. As such, the external device 804 is configured to transfer data (and potentially power) to the vestibular stimulator 812.

The vestibular stimulator 812 comprises an implant body (main module) 834, a lead region 836, and a stimulating assembly 816, all configured to be implanted under the skin/tissue (tissue) 815 of the user. The implant body 834 generally comprises a hermetically-sealed housing 838 in which RF interface circuitry, one or more rechargeable batteries, one or more processors, and a stimulator unit are disposed. The implant body 134 also includes an internal/implantable coil 814 that is generally external to the housing 838, but which is connected to the transceiver via a hermetic feedthrough (not shown).

The stimulating assembly 816 comprises a plurality of electrodes 844(1)-(3) disposed in a carrier member (e.g., a flexible silicone body). In this specific example, the stimulating assembly 816 comprises three (3) stimulation electrodes, referred to as stimulation electrodes 844(1), 844(2), and 844(3). The stimulation electrodes 844(1), 844(2), and 844(3) function as an electrical interface for delivery of electrical stimulation signals to the user's vestibular system.

The stimulating assembly 816 is configured such that a surgeon can implant the stimulating assembly adjacent the user's otolith organs via, for example, the user's oval window. It is to be appreciated that this specific embodiment with three stimulation electrodes is merely illustrative and that the techniques presented herein may be used with stimulating assemblies having different numbers of stimulation electrodes, stimulating assemblies having different lengths, etc.

Shown in FIG. 8 is a cross-sectional view of an accessory device 862, in accordance with embodiments presented herein. Similar to the above embodiments, the accessory device 862 is configured to transfer heat from the external device 804, operating in an insulated environment, to a non-insulated environment. Accessory device 862 can be similar to one or more of the above described accessory devices 362 or 462, or can have an alternative configuration selected for a specific operational arrangement.

As previously described, the technology disclosed herein can be applied in any of a variety of circumstances and with a variety of different devices. While the above-noted disclosure has been described with reference to medical device, the technology disclosed herein may be applied to other electronic devices that are not medical devices. For example, this technology may be applied to, e.g., ankle or wrist bracelets connected to a home detention electronic monitoring system, or any other chargeable electronic device worn by a user.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

According to certain aspects, systems and non-transitory computer readable storage media are provided. The systems are configured with hardware configured to execute operations analogous to the methods of the present disclosure. The one or more non-transitory computer readable storage media comprise instructions that, when executed by one or more processors, cause the one or more processors to execute operations analogous to the methods of the present disclosure.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

It is also to be appreciated that the embodiments presented herein are not mutually exclusive and that the various embodiments may be combined with another in any of a number of different manners.

What is claimed is:

1. An accessory device for an external component that is configured to transfer power to an implantable device, wherein the external component is configured to be at least partially located within an insulated environment abutting a body of a user, the accessory device comprising:

a thermally conductive main body configured to be positioned abutting a housing of the external component within the insulated environment to receive heat generated by the external component; and a thermally conductive extension extending from the thermally conductive main body, wherein the thermally conductive extension is configured to transfer heat from the thermally conductive main body to a location outside of the insulated environment.

2. The accessory device of claim 1, wherein the accessory device is physically separate from the external component.

3. The accessory device of claim 1, wherein the thermally conductive main body and the thermally conductive extension are integrated in a head covering.

4. The accessory device of claim 3, wherein the head covering is at least one of a helmet, a scarf, or a hat.

5. The accessory device of claim 1, wherein the accessory device further comprises a headband attached to at least one of the thermally conductive main body or the thermally conductive extension.

6. The accessory device of claim 5, wherein the headband is formed from a thermally conductive material.

7. The accessory device of claim 1, wherein the thermally conductive extension comprises a headband attached to the thermally conductive main body.

8. The accessory device of claim 1, wherein the thermally conductive main body and the thermally conductive extension are integrated.

9. The accessory device of claim 1, wherein at least one of the thermally conductive main body or the thermally conductive extension comprises a thermally conductive foam.

10. The accessory device of claim 1, wherein at least one of the thermally conductive main body or the thermally conductive extension comprises one or more heat pipes.

11. The accessory device of claim 1, wherein at least one of the thermally conductive main body or the thermally conductive extension comprises an electrically non-conductive material.

12. The accessory device of claim 1, wherein the thermally conductive main body comprises an aperture configured to receive the external component therein.

13. An apparatus comprising:

a thermally conductive member having at least a thermally conductive first part configured to be in contact with a housing of an external charger that is configured to be worn by a user and transfer power to an implantable device, wherein use of the external charger thermally insulates the housing of the external charger between a body of a user and a covering member, wherein the thermally conductive member comprises at least a thermally conductive second part configured to transfer heat from the thermally conductive first part to a non-insulated environment outside of the covering member.

14. The apparatus of claim 13, wherein the apparatus is physically separate from the external charger.

15. The apparatus of claim 13, wherein the thermally conductive member is integrated in a head covering.

16. The apparatus of claim 13, wherein the apparatus further comprises a headband attached to at least one of the thermally conductive first part or the thermally conductive second part.

17. The apparatus of claim 16, wherein the headband is formed from a thermally conductive material.

18. The apparatus of claim 13, wherein the thermally conductive second part comprises a headband attached to the thermally conductive first part.

19. The apparatus of claim 13, wherein at least one of the thermally conductive first part or the thermally conductive second part comprises at least one of a thermally conductive foam or one or more heat pipes.

20. A method comprising:

positioning a thermally conductive body abutting a wearable device, wherein the wearable device is configured to be worn by a user, and wherein, when worn by the user, the wearable device is placed in a thermally insulated environment abutting a body of the user;

receiving, by the thermally conductive body, heat generated by the wearable device during operation of the wearable device;

transferring the heat from the thermally conductive body to a thermally conductive extension that includes a portion located outside of the thermally insulated environment; and expelling the heat received from the thermally conductive body to a location outside of the thermally insulated environment.

21. The method of claim 20, wherein transferring the heat from the thermally conductive body to a thermally conductive extension comprises:

transferring the heat to a thermally conductive headband extending to a location outside of the thermally insulated environment.

22. The method of claim 20, wherein transferring the heat from the thermally conductive body to a thermally conductive extension comprises:

transferring the heat to one or more heat pipes extending to a location outside of the thermally insulated environment.

23. The method of claim 20, wherein at least one of the thermally conductive body or the thermally conductive extension comprises a thermally conductive foam or one or more heat pipes.

24. The method of claim 20, wherein at least one of the thermally conductive body or the thermally conductive extension comprises an electrically non-conductive material.

25. The method of claim 20, wherein the thermally conductive body comprises an aperture configured to receive the wearable device therein.

* * * * *